(12) United States Patent
Kennedy et al.

(10) Patent No.: US 8,889,926 B2
(45) Date of Patent: Nov. 18, 2014

(54) METHOD FOR THE SYNTHESIS OF LOW COST INITIATORS FOR TELECHELIC POLYISOBUTYLENES

(75) Inventors: Joseph P. Kennedy, Akron, OH (US); Gabor Erdodi, Macedonia, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/130,079

(22) PCT Filed: Jul. 2, 2012

(86) PCT No.: PCT/US2012/045201
§ 371 (c)(1),
(2), (4) Date: Apr. 7, 2014

(87) PCT Pub. No.: WO2013/003838
PCT Pub. Date: Jan. 3, 2013

(65) Prior Publication Data
US 2014/0235905 A1      Aug. 21, 2014

Related U.S. Application Data

(60) Provisional application No. 61/502,919, filed on Jun. 30, 2011.

(51) Int. Cl.
| | | |
|---|---|---|
| *C07C 17/16* | (2006.01) | |
| *C07C 17/35* | (2006.01) | |
| *C07C 29/132* | (2006.01) | |
| *C07C 2/86* | (2006.01) | |
| *C07C 407/00* | (2006.01) | |
| *C07C 15/02* | (2006.01) | |
| *C08F 110/10* | (2006.01) | |
| *C07C 22/04* | (2006.01) | |
| *C08F 110/00* | (2006.01) | |

(52) U.S. Cl.
CPC .............. *C07C 17/16* (2013.01); *C07C 17/35* (2013.01); *C07C 29/132* (2013.01); *C07C 2/861* (2013.01); *C07C 407/00* (2013.01); *C07C 15/02* (2013.01); *C08F 110/00* (2013.01); *C08F 110/10* (2013.01); *C07C 2527/128* (2013.01); *C07C 22/04* (2013.01)
USPC .......................................... 570/201; 570/190

(58) Field of Classification Search
CPC ............................... C07C 17/16; C07C 17/35
USPC ................................................ 570/201, 190
See application file for complete search history.

(56) References Cited

U.S. PATENT DOCUMENTS

| | | |
|---|---|---|
| 2,888,485 A | 5/1959 | Bailey |
| 3,787,358 A | 1/1974 | Nighioka et al. |
| 4,767,885 A | 8/1988 | Kennedy |
| 2007/0197838 A1 | 8/2007 | Seino |

*Primary Examiner* — Elvis O Price
(74) *Attorney, Agent, or Firm* — Renner Kenner Greive Bobak Taylor & Weber

(57) ABSTRACT

A method for the synthesis of 1,3-di(chloropropyl)-5-tert-butyl benzene includes the steps of conducting Friedl-Crafts alkylation of 1,3-diisopropyl benzene by tert-butyl chloride in the presence of an alkylation catalyst to obtain 1-tert-butyl-3,5-diisopropylbenzene; peroxidizing the 1-tert-butyl-3,5-diisopropyl benzene by gaseous oxygen in the presence of a peroxidation catalyst in a basic solution to obtain 1,3-di(peroxypropyl)-5-tert-butylbenzene; reducing the 1,3-di(peroxypropyl)-5-tert-butylbenzene with a reducing agent to 1,3-di(hydroxylpropyl)-5-tert-butylbenzene; and chlorinating the 1,3-di(hydroxypropyl)-5-tert-butylbenzene to obtain 1,3-di(chloropropyl)-5-tert-butyl benzene.

10 Claims, 4 Drawing Sheets

METHOD FOR THE SYNTHESIS OF LOW COST INITIATORS FOR TELECHELIC POLYISOBUTYLENES

CROSS-REFERENCE TO RELATED APPLICATIONS

This application claims the benefit of U.S. Provisional Patent Application No. 61/502,919, filed Jun. 30, 2011.

TECHNICAL FIELD

The present invention relates to a new method for synthesizing known di-functional carbocationic initiators, such as 1,3-di(chloropropyl)-5-tert-butylbenzene, referred to sometimes herein as "tBu[Cl]$_2$". More particularly, the present inventions relates to a new peroxidation-based synthesis of the known difunctional initiator, tBu[Cl]$_2$ wherein the method includes the synthesis of 1-tert-butyl-3-5-diisopropylbenzene (tBu[iPr]$_2$ from 1,3-diisopropylbenzene and inexpensive inorganic reagents. Compositions made from those methods are also claimed.

BACKGROUND FOR THE INVENTION

The invention of living carbocationic polymerizations, specifically that of isobutylene, was a milestone in synthetic polymer science because, in addition to a synthetic breakthrough, it lead to the development of several commercially significant products. One of these products is telechelic polyisobutylene (F-PIB-F, where F=functional group, PIB=polyisobutylene), the enabling intermediate of poly(styrene-b-isobutylene-b-styrene) (SIBS), the drug eluting coating on Boston Scientific's Taxus® coronary stent implanted in and enhancing the quality of life of millions of people!

A cost analysis of the product revealed that up to 90% of the cost of the commercially significant low molecular weight (defined herein as Mn~3000 g/mol or less) telechelic polyisobutylene is due to the "blocked" initiator 1,3(2-methoxy-2-propyl)-5-tert butylbenzene (hereinafter "tBuDiCumMeO") employed for its synthesis. The reasons for using this specific structure are well known, but to date, no other structures have been commercially available and/or commercially successful for the specific use as a polymerization initiator for the specific living carbocationic polymerizations desired.

In fact, heretofore, only one other attempt, (see Applicants' of record co-pending PCT Application No. PCT/US11/68104) has been known to have been made to produce other polymerization initiators that are far less expensive and just as efficient as the initiator, tBuDiCumMeO. However, even that relatively new synthesis of, for example, 1,3-di(2-methoxy-2-propyl)-5-isopropyl benzene (also noted sometimes hereinafter as "iPrDiCum MeO"), is believed to be far more expensive than necessary, and more expensive that the synthesized compounds provided in this disclosure. This is because, in order to use an isopropyl group-containing initiator rather than tert-butyl group-containing initiator, the new isopropyl group-containing initiator would require FDA approval as a polyisobutylene(PIB)-based biomaterial. Under FDA guidelines, the isopropyl group initiator residue contained in the PIB would need to be tested and approved before use as a biomaterial. The high cost of testing to obtain FDA approval of the isopropyl group-containing initiator could be problematic to its commercial success in the growing industry of initiators for carbocationic polymerizations.

Thus, a need still exists for a simple low cost synthesis for other polymerization initiators, particularly those containing a tert-butyl residues, which will not require FDA approval. Given the relative expense in the preparation and use of tBuDiCumMeO initiators for the production of telechelic polyisobutylenes, and the fact that isopropyl group-containing initiators must still obtain FDA approval, the need continues to exist for methods of synthesizing other functionally efficient, low cost initiators containing tert-butyl residues, whether well-known or not.

SUMMARY OF THE INVENTION

Any one or more of the foregoing aspects of the present invention, together with the advantages thereof over known art relating to polymerization initiators and the methods of synthesis of the same, which will become apparent from the specification that follows, may be accomplished by the invention as hereinafter described and claimed.

The present invention provides a new method for the synthesis of 1,3-di(chloropropyl)-5-tert-butylbenzene, a well known difunctional carbocationic initiator. The synthesis is novel in that, among other things, it provides, as a first step, conducting a Friedl-Crafts alkylation of 1,3-diisopropylbenzene by tert-butyl chloride in the presence of an alkylation catalyst, such as, for example, an iron(III) salt such as FeCl$_3$. This alkylation reaction creates the reaction product 1-tert-butyl-3,5-diisopropylbenzene, which then undergoes, as a second step of the synthesis, peroxidation. Peroxidization of the 1-tert-butyl-3,5-diisopropyl benzene is done to obtain 1,3-di(peroxypropyl)-5-tert-butylbenzene. The 1-tert-butyl-3,5-diisopropylbenzene is peroxidized by gaseous oxygen in the presence of a peroxidation catalyst in a basic solution to obtain the 1,3-di(peroxypropyl)-5-tert-butylbenzene. In any embodiment described herein, the catalyst in the basic solution may be a Cobalt(II) salt and a tertiary amine in water. Further, in any embodiment described herein, the cobalt(ii) salt may be CoCl$_2$ and the tertiary amine may be pyridine. Still further, in any embodiments described herein, the step of peroxiding may further include the steps of adjusting a pH of the 1,3-di(peroxypropyl)-5-tert-butylbenzene in solution with the addition of a base solution to a pH of about 10; and extracting the water phase with ether to provide a mixture containing 1,3-di(peroxypropyl)-5-tert-butylbenzene dissolved in ether.

In a third step of the synthesis process, the 1,3-di(peroxypropyl)-5-tert-butylbenzene is reduced to 1,3-di(hydroxypropyl)-5-tert-butylbenzene with a reducing agent. In any embodiments described herein, the reducing agent may be sodium sulfite. Further, in any embodiments described herein, the step of reducing may further include the steps of reducing the mixture containing 1,3-di(peroxypropropyl)-5-tert-butylbenzene dissolved in ether with sodium sulfite to provide 1,3-di(hydroxypropyl)-5-tert-butylbenzene, then separating and extracting the water with additional ether; and evaporating and drying the 1,3-di(hydroxypropyl)-5-tert-butylbenzene. Still further, in any embodiments described herein, the step of reducing may further include washing with hexane and recrystallizing with ethyl acetate, the 1,3-di(hydroxypropyl)-5-tert-butylbenzene.

Chlorination of 1,3-di(hydroxypropyl)-5-tert-butylbenzene may then be conducted to obtain the desired difunctional carbocationic initiator, 1,3-di(chloropropyl)-5-tert-butylbenzene. In any embodiments described herein, the step of chlorinating may include dissolving the 1,3-di(hydroxypropyl)-5-tert-butylbenzene in methyl chloride to provide a solution and bubbling the solution in HCl. Further, in any embodiment described herein, the step of chlorinating may further includes purifying the 1,3-di(chloropropyl)-5-tert-butyl benzene by evaporating and recrystallizing the 1,3-di(chloropropyl)-5-tert-butyl benzene in hexane.

Another aspect of the present invention provides a novel composition of matter, namely, 1,-tert-butyl-3,5-diisopropylbenzene. This composition has heretofore never been used as an intermediate for the synthesis of a carbocationic initiator such as, for example, 1,3-di(chloropropyl)-5-tert-butyl benzene.

A further aspect of the present invention provides a composition of 1,3-di(chloropropyl)-5-tert-butyl benzene made by any of the embodied methods disclosed herein.

Yet another aspect of the present invention provides a polymerization initiator comprising 1,3-di(chloropropyl)-5-tert-butyl benzene synthesized by any of the embodied methods disclosed herein and having a purity of at least 50%.

Beneficially, it will be appreciated that, from the synthesis of these compositions, namely, 1,3-di(chloropropyl)-5-tert-butylbenzene, low cost polymerization initiators may be produced that are highly desirable and efficient in carrying out living carbocationic polymerizations. That is, polymerization initiators suitable for use in the preparation of living carbocationic polymers, such as, for example, telechelic (e.g., ditelechelic) polyisobutylenes, can be synthesized.

DESCRIPTION OF ONE OR MORE DETAILED EMBODIMENTS

The present invention provides for a new low cost method for synthesizing a desirable and efficient polymerization initiator for living carbocationic polymerizations. Specially, a new method for the synthesis of 1-tert-butyl-3,5-bis(2-chloropropan-2-yl)benzene, or as alternatively stated, 1,3-di (chloropropyl)-5-tert-butylbenzene (hereinafter sometimes referred to as "tBu[Cl]$_2$") is provided. It will be appreciated that 1,3-di(chloropropyl)-5-tert-butylbenzene is, more specifically, 1,3-di(2-chloropropyl)5-tert-butybenzene, but that it is to be understood that the chloro group, or any other group (e.g., peroxy, hydroxy) will have the active group in the 2 position unless otherwise stated. This product is well-known as a difunctional carbocationic initiator, but has never been easily synthesized, and never made by the method disclosed herein. More particularly, the new method utilizes an inexpensive simple starting material, 1,3-diisopropylbenzene, and cheap inorganic reagents to give intermediates that, upon Friedl-Crafts, alkylation, peroxidation, reduction and chlorination, results in the production of tBu[Cl]$_2$ with good yields and high purity.

In doing so, a novel composition has been developed as an intermediate. The new intermediate composition, produced by the Friedl-Crafts alkylation of 1,3-diisopropylbenzene by tert-butyl chloride results in the production of 1-tert-butyl-3,5-diisopropylbenzene. The compound can then be used as the starting material for the peroxidation-based reaction as disclosed herein to provide the di-functional carbocationic initiator, 1,3-di(chloropropyl)-5-tert butylbenzene (tBu[Cl]$_2$).

In order to understand the synthesis of the compositions, it will be appreciated that Scheme 1 hereinbelow provides one detailed embodiment of a suitable reaction scheme for the present invention. It will be appreciated that Scheme 1 below outlines the synthesis route for obtaining 1,3-di(chloropropyl)-5-tert butylbenzene (referred to herein and the Scheme 1 as "tBu[Cl]$_2$").

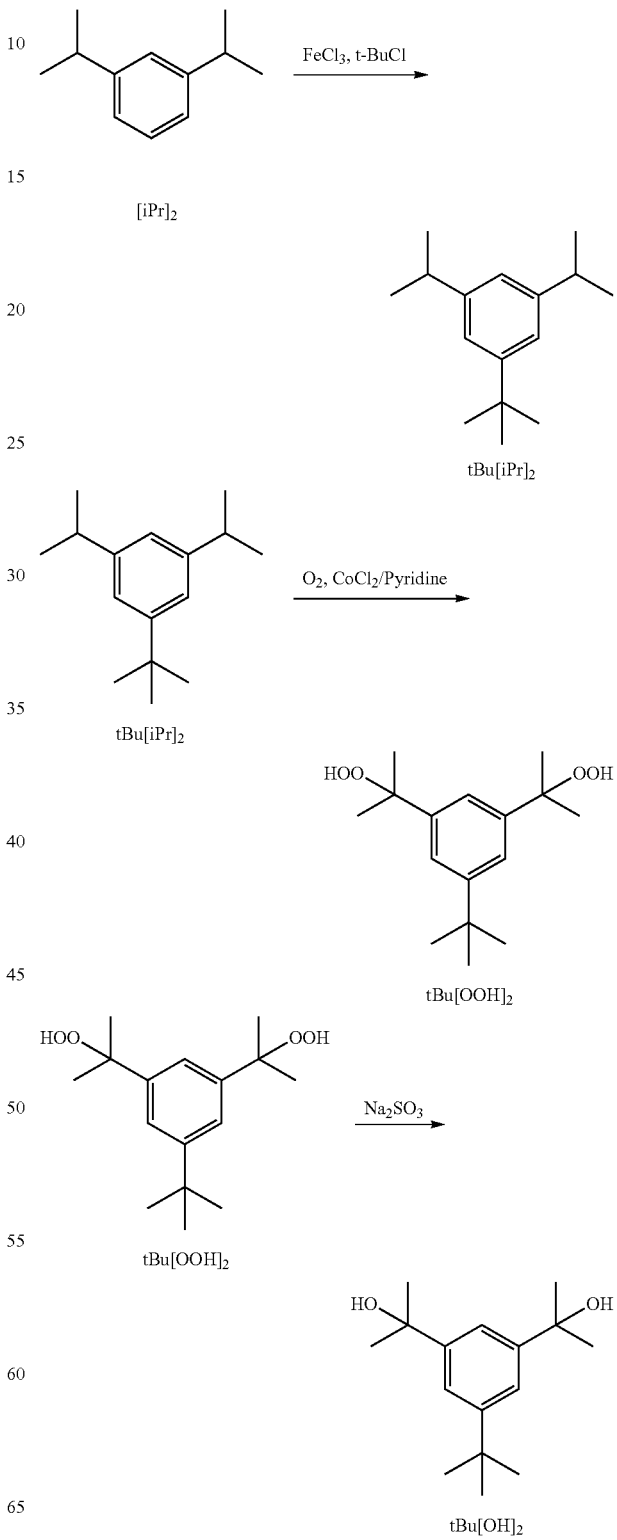

-continued

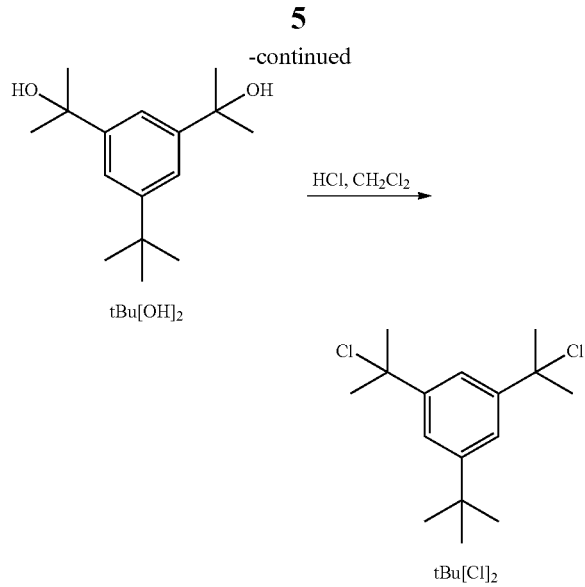

The method for synthesizing 1,3-di(chloropropyl)-5-tert-butylbenzene comprises, as a first step, conducting a Friedl-Crafts alkylation of 1,3-diisopropylbenzene (referred to in Scheme 1 as "[iPr]$_2$") by tert-butyl chloride (t-BuCl) in the presence of an alkylation catalyst. Examples of such an alkylation catalyst suitable for use are those iron(III) salts such as, for example, FeCl$_3$.

Figure 1:
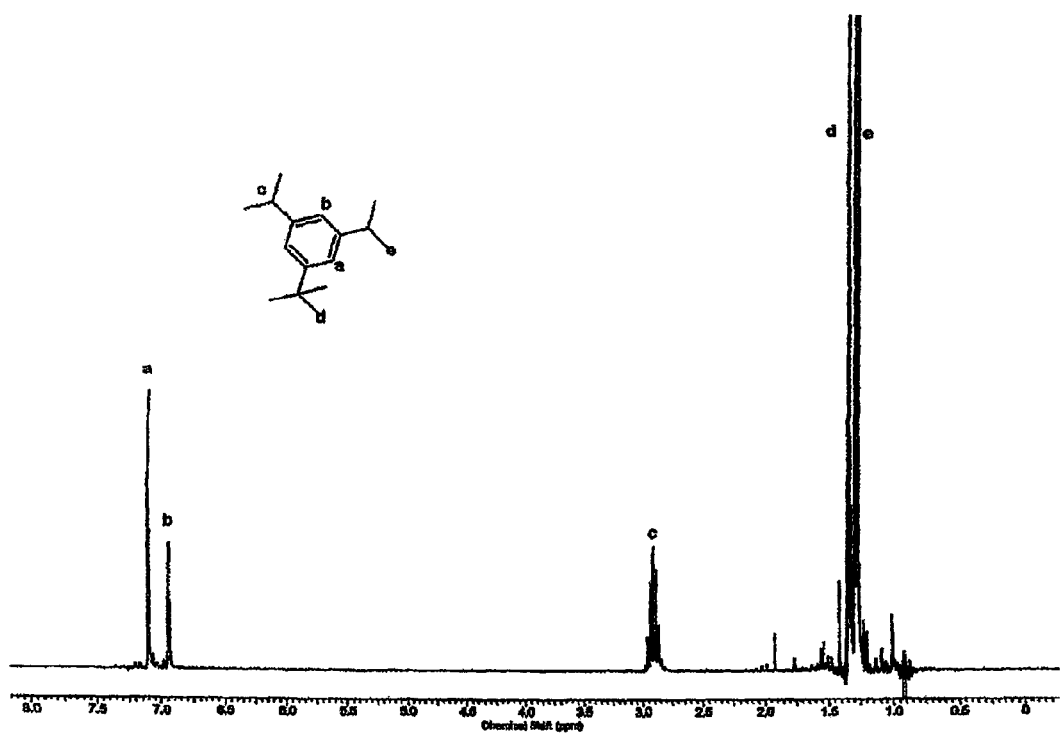
FIG. 1 is a 1H NMR spectrum of 1-tert-butyl-3,5-diisopropylbenzene.

This alkylation reaction creates the reaction product 1-tert-butyl-3,5-diisopropylbenzene (referred to in Scheme 1 and sometimes hereinafter as "tBu[iPr]$_2$"). The electrophilic substitution takes place in the meta positions relative to the isopropyl groups. Notably and importantly, ortho-substitution does not occur due to steric hindrance. The reaction can be carried out with excess 1,3-diisopropylbenzene to minimize side reactions due to rearrangements of the reactive tBu$^+$ cation. Any unreacted 1,3-diisopropyl benzene can be easily separated from the resultant reaction product mixture by vacuum distillation or rectification, as is well known in the art. FIG. 1 shows a 1H NMR spectrum of one tested sample of the reaction product tBu[iPr]$_2$ made by the method described herein.

The second step of the synthesis is the peroxidation of 1-tert-butyl-3,5-diisopropylbenzene (tBu[iPr]$_2$) to obtain 1,3-di(peroxypropyl)-5-tert-butylbenzene (referred to in Scheme 1 and sometimes hereinafter as "tBu[OOH]$_2$"). The 1-tert-butyl-3,5-diisopropylbenzene is peroxidized by gaseous oxygen in the presence of a peroxidation catalyst in a basic solution to obtain the 1,3-di(peroxypropyl)-5-tert-butylbenzene.

In one embodiment, the de facto catalysts are cobalt (II) oxide/hydroxide complexes that form in situ from CoCl$_2$ under basic conditions during O$_2$ bubbling. Although the catalyst particles are insoluble in water, they remain dispersed in the aqueous phase. The reaction may be carried out in the presence of pyridine as co-catalyst and improves the adsorption of the reactants on the catalyst particles. The pH of the solution strongly influences both the yield and reaction rate. At low pH, the reaction is rapid but the yield of peroxides decreases because other oxidized byproducts are also formed. It was found that pH=10 is optimal for the synthesis. The medium becomes slowly acidic due to the formation of peroxides. To avoid undesirable pH changes, the pH was adjusted periodically by KOH and, in another embodiment, a small amount of Na$_2$HPO$_4$ buffer was added with the KOH.

In this or other embodiments, the reaction product became a viscous slurry mixture. Therefore, the viscous slurry of the reaction product was separated from the water phase by a separatory funnel. The water phase was extracted with ether. The reaction product slurry mixture was dissolved in ether and was used in the reduction step without further purification.

Figure 2:
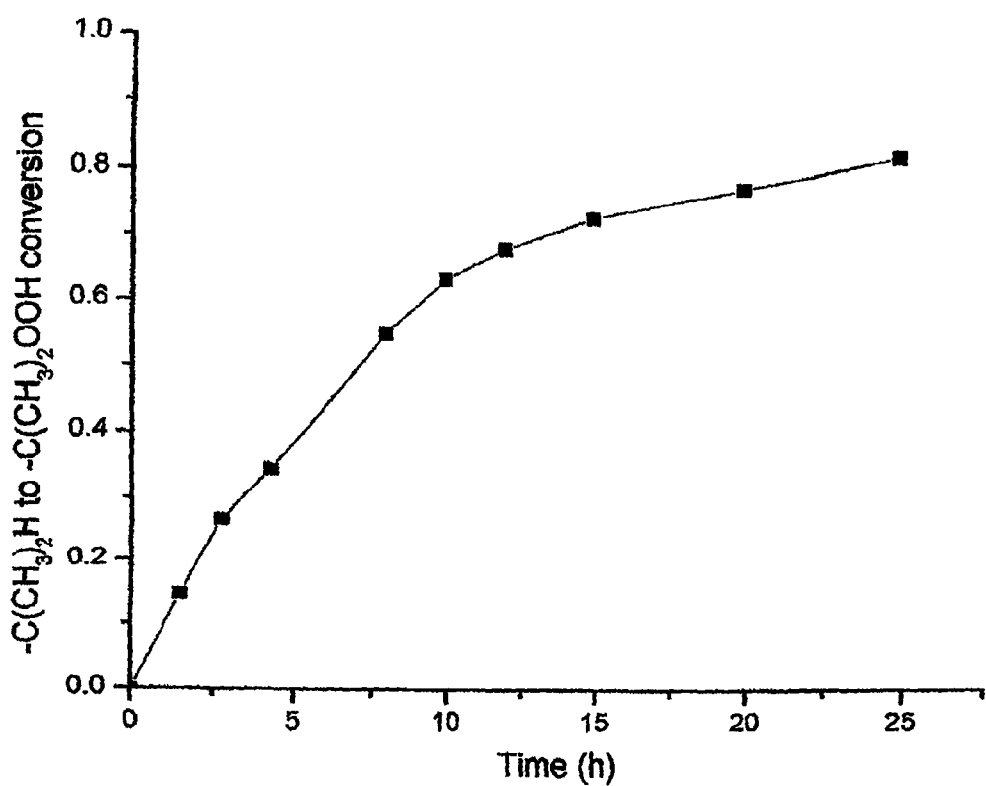
FIG. 2 is a graph of the conversion of the peroxidation of 1-tert-butyl-3,5-diisopropylbenzene as a function of time.

FIG. 2 shows conversion of tBu[iPr]$_2$ to tBu[OOH]$_2$. At longer reaction times, the peroxidation rate decreases, and after 24 hours, it has been found that reaction has obtained at least an 80% conversion. In other embodiments, it has been found that after 24 hours, the reaction obtained at least an 83% conversion.

Figure 3:
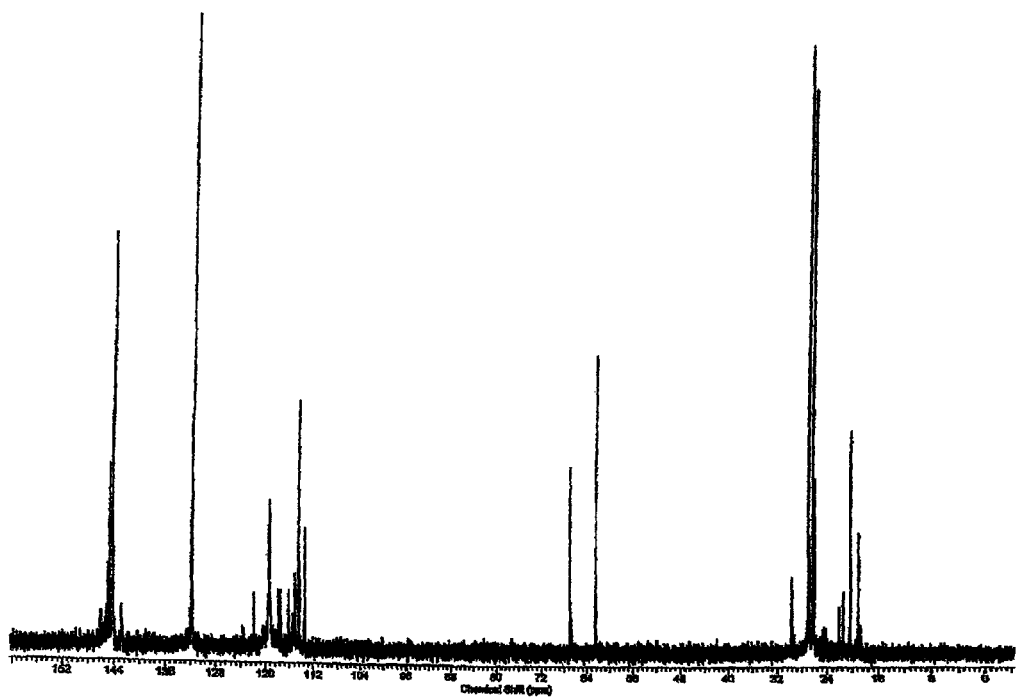
FIG. 3 is a C13 NMR spectrum of the mixture obtained after the reduction of 1,3-di(peroxypropyl)-5-tert-butylbenzene to 1,3-di(hydroxypropyl)-5-tert-butylbenzene.
Figure 4:
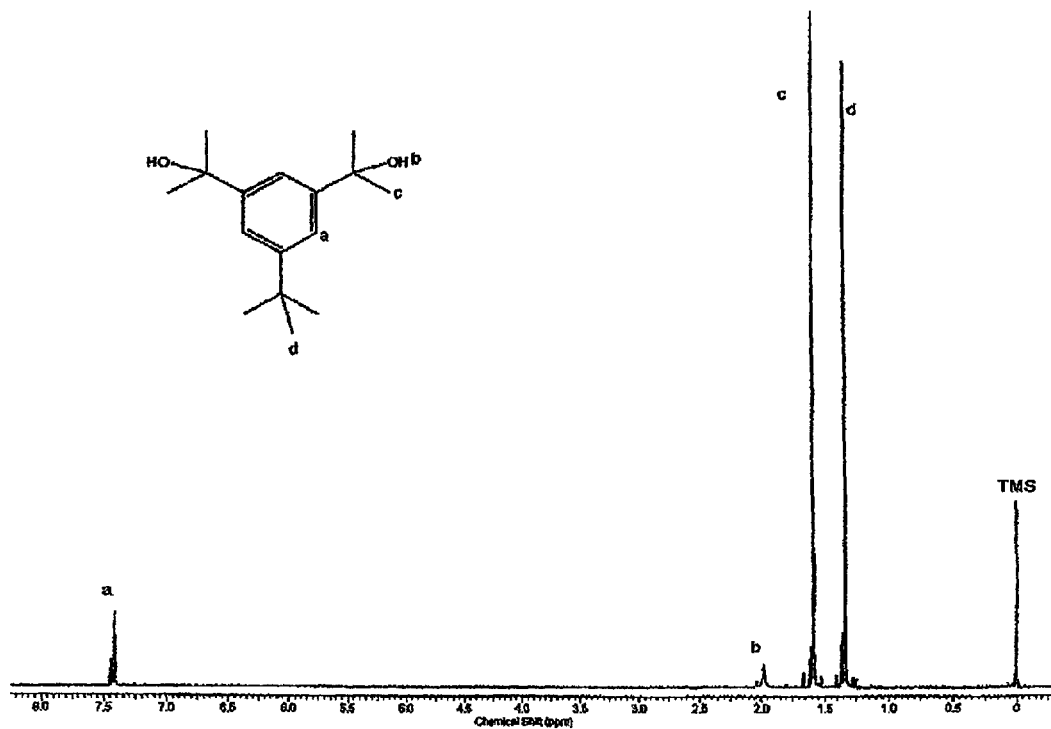
FIG. 4 is a 1H NMR spectrum of purified 1,3-di(hydroxypropyl)-5-tert-butylbenzene.

After peroxidation to tBu[OOH]$_2$, reduction of tBu[OOH]$_2$ was carried out, by way of one or more known processes for reducing organic mixtures, to obtain 1,3-di(hydroxypropyl)-5-tert-butylbenzene (referred to in Scheme 1 and sometimes hereinafter as "tBu[OH]$_2$"). In one embodiment, tBu[OOH]$_2$ may be reduced using sodium sulfite (Na$_2$SO$_3$). The reduction may take place in water at room temperature. In another or the same embodiment, to avoid autoaccerlerating self-oxidation of the peroxides, the tBu[OOH]$_2$ may be added dropwise to a slightly acidic or neutral sodium sulfite solution so that no reaction occurs. Again, amounts of reducing agent needed for carrying out this reaction will be known to those skilled in the art and can be carried out without undue experimentation. FIG. 3 provides a $^{13}$C NMR spectroscopy confirming the complete reduction of the peroxides to hydroxyl groups (i.e., tBu[OOH]$_2$ to tBu[OH]$_2$). The isolation of tBu[OH]$_2$ was more simple than the isolation of the 5-isopropyl difunctional (iPrDiCum MeO) initiator, because of the lack of solid byproducts. That is, tBu[OH]$_2$ readily crystallizes from the product mixture and yields nearly pure product which can be further purified by crystallization from ethyl acetate. FIG. 4 shows a 1H NMR spectrum of a tested sample of tBu[OH]$_2$ made by the method described herein. tBu[OH]$_2$ is a white powder.

In one or more embodiments, the method may, more specifically, continue by separating the 1,3-di(hydroxypropyl)-5-tert-butylbenzene (tBu[OH]2) from the water phase by extracting the water phase with additional ether. The combined organic phase may be washed with solution such as NaHCO$_3$ and dried over MgSO$_4$ or similar well known drying products. Finally, the solvents can be evaporated and the product dried, such as, for example and in one embodiment, in vacuum for 24 hours at room temperature. Upon drying, the tBu[OH]$_2$ crystallizes out of the liquid. The crystals may be filtered, washed with hexanes and recrystallized in ethyl acetate.

After reduction, tBu[OH]$_2$ can be chlorinated as is well known in the art to provide the desired resultant product, 1,3-di(chloropropyl)-5-tert-butylbenzene, (referred to in Scheme 1 and sometimes referred to herein as "tBu[Cl]$_2$"). In one embodiment, tBu[Cl]$_2$ can be dissolved in methylene chloride with, optionally, CaCl$_2$ being added. During stirring HCl can be bubbled into the solution for a set period of time and at a set temperature, e.g., 30 minutes at 0° C. Then, the solution can be filtered. The solvents may be evaporated, and the product recrystallized in hexanes. Such a method has been tested and provides pure 1,3-di(chloropropyl)-5-tert-butylbenzene as determined by NMR spectroscopy. Test has shown that the product has at least a 50% yield, and in one embodiment has at least a 54% and, in another embodiment, a 60% yield.

It will be appreciated that the resultant composition, tBu[Cl]$_2$ can be used as a suitable polymerization initiator for the preparation of telechelic polyisobutylenes. Reaction of the intiator tBu[Cl]$_2$ with isobutylene can be carried out as well known in the art for such living carbocationic polymerizations. The preparation of such telechelic polyisobutylenes are well known and have been described throughout the literature.

In order to demonstrate practice of the invention, the method described above and as set forth in Scheme 1 was used to prepare the composition 1,3-di(chloropropyl)-5-tert-butylbenzene. In preparation for conducting the method, 1,3-diisopropylbenzene, tert-butyl chloride, FeCl$_3$, CoCl$_2$.6H$_2$0, pyridine, Na$_2$HPO$_4$.7H$_2$0, KOH, HCl gas and Na$_2$S0$_3$ was obtained from Aldrich, tetrahydrofuran, diethyl ether, hexanes, methanol, CH$_2$Cl$_2$, NaHCO$_3$, MgSO$_4$ and sulfuric acid was obtained from Fischer, and isobutylene and oxygen was obtained from Praxair.

All 1H and C13 NMR spectra were obtained by a Varian Mercury 300 MHz NMR spectrometer in deuterated chloroform solutions. GPC eluograms, where used, were obtained with a Waters GPC instrument equipped with a series of six Waters Styragel columns (HR 0.5, HR 1, HR 3, HR 4, HR 5, and HR 6) and a refractive-index detector (Optilab, Wyatt Technology). Samples were dissolved in THF, and the flow rate was 1 mL THF/min. Molecular weights were calculated by the use of polystyrene standards. Gas chromatograms, where used, were obtained by a Shimadzu instrument equipped with an Equity-1 fused silica capillary column, a TCD detector, and a CR501 recorder using He as carrier gas.

As presented in Scheme 1 and generally explained above, one representative embodiment for carrying out the synthesis of 1,3-di(chloropropyl)-5-tert-butylbenzene is described and carried out in the following detailed steps.

Synthesis of 1-tert-butyl-3,5-diisopropylbenzene (tBu[iPr]$_2$)

To 1,3-diisopropylbenzene (300 mL, 252 g, 1.55 mol) and FeCl$_3$ (50 g, 0.31 mol), tert-butyl chloride (100 mL, 87 g, 0.773 mol) was added dropwise at 0° C. in 20 minutes. After 1 hour, the product was extracted with water and NaHCO$_3$ solution, dried over CaCl$_2$ and distilled in vacuum at 0.5 mbar pressure. Two fractions were collected, the fraction at 46° C. was 1,3-diisopropylbenzene (99 g, 0.61 mol), the fraction at 63° C. was pure 1-tert-butyl-3,5-diisopropylbenzene (96 g, 0.41 mol). The product is a clear liquid, and had a yield of 46% (adjusted with 1,3-diisopropylbenzene recycling: 0.41 mol/(1.55 mol-0.61 mol)).

Synthesis of 1,3di(peroxypropyl)-5-tert-butyl-benzene (tBu[OOH]$_2$)

In a 3 neck 1 L flask equipped with a condenser, a mechanical stirrer and a gas inlet CoCl$_2$×6H$_2$O (15 g, 0.063 mol) and pyridine (30 g, 0.38 mol) was dissolved in 200 mL water. In a beaker, KOH (7 g, 0.125 mol) and Na$_2$HPO$_4$×7H$_2$O (20 g, 0.075 mol) were dissolved in 200 mL water and added to the flask together with 1-tert-butyl-3,5-diisopropylbenzene (96 g, 0.44 mol) during stirring. Oxygen was bubbled into the solution at about 30 L/hour. The solution was heated to 90-95° C. and was stirred at 300 rpm for 24 hours. During the peroxidation the pH was monitored and adjusted to pH=10 by the addition of KOH solution. The viscous slurry of the product mixture was separated from the water phase in a separatory funnel. The water phase was extracted with 2-300 mL ether. The mixture was dissolved in ether and was used in the next step without further purification.

Synthesis of 1,3di(hydroxypropyl)-5-tert-butylbenzene (tBu[OH]$_2$)

Into a 3 neck 1 L flask equipped with a mechanical stirrer and a thermometer 190 g Na$_2$SO$_3$ and 500 mL water were added. The solution was cooled to 10-20° C. and the pH was set to pH=6. The ether solution of 1,3-di(2-peroxypropyl)-5-tert-butylbenzene obtained in the previous step was added during strong stirring to the aqueous Na$_2$SO$_3$ solution at pH=6-7 in 30 min at 10-20° C. and. Then the solution was stirred for an additional 30 minutes at room temperature. The organic phase was separated, the water phase was extracted with additional ether, and the combined organic phase was washed with NaHCO$_3$ and dried over MgSO$_4$. Finally, the solvents were evaporated and the product was dried in vacuum for 24 hours at room temperature. During drying, the 1,3-di(2-hydroxypropyl)-tert-butylbenzene crystallized out of the liquid. The crystals were filtered, washed with hexanes and recrystallized in ethyl acetate. The product, 1,3-di(2-hydroxypropyl)-5-tert-butylbenzene, is a white powder (28 g, yield: 26%).

Synthesis of 1,3-di(cholorpropyl)-5-tert-butylbenzene (tBu[Cl]$_2$)

1,3-di(hydroxypropyl)-5-tert-butylbenzene (28 g, 0.22 mol) was dissolved in methylene chloride and 25 g CaCl2 were added. During stirring, HCl was bubbled into the solution at 0° C. for 30 minutes. Then solution was filtered, the solvents were evaporated and the product was recrystallized in hexanes. The product was pure 1,3-di(chloropropyl)-5-tert-butylbenzene as determined by NMR spectroscopy (35 g, yield 54%).

As a result of this method, tests were conducted to confirm the compositions obtained. One desirable aspect of the present invention was the synthesis of a new intermediate compound, to the initiator, 1-tert-butyl-3,5-diisopropylbenzene, (abbreviated tBu[iPr]$_2$ in Scheme 1). Another desirable aspect of the present invention was the new, low cost method of synthesis of tBu[Cl]$_2$ for the preparation of telechelic polyisobutylenes by living carbocationic polymerization. This new synthesis preserves the tert-butyl group as the blocking substituent in the 1 (or 5) position on the aromatic ring to prevent intramolecular alkylation by steric inhibition during carbocationic polymerization of the commonly used initiator tBu[Cl]$_2$, thus avoiding additional FDA approval.

The efficacy of tBu[Cl]$_2$ as an initiator for the carbocationic polymerization of isobutylene to well-defined telechelic polyisobutylene has been experimentally demonstrated and is well known in the art and has not been shown here, but examples of similar experiments using, for example, iPrDi-Cum MeO, have been carried out in the art and in Applicant of record's co-pending PCT Application No. PCT/US11/68104, the disclosure of which is incorporated herein by reference. Such experiments are now routinely carried out under well-established polymerization conditions and polymer characterization methods.

In light of the foregoing, the difunctional initiator 1,3-di (chloropropyl)-5-tert-butylbenzene (tBu[Cl]$_2$) has been synthesized for use as "blocked" initiators for the preparation of telechelic polyisobutylenes by living carbocationic polymerization. An intermediate compound, tBu[iPr]$_2$, is unique to this method of synthesis and is, therefore, believed novel as well. The method is desirably low cost relative to the high price of compositions currently used in the preparation of telechelic polyisobutylenes.

Although the present invention has been described in considerable detail with reference to certain embodiments, other embodiments are possible. Therefore, the spirit and scope of the appended claims should not be limited to the description of the embodiments contained herein.

What is claimed is:

1. A method for the synthesis of 1,3-di(chloropropyl)-5-tert-butyl benzene comprising:
   conducting Friedl-Crafts alkylation of 1,3-diisopropylbenzene by tert-butyl chloride in the presence of an alkylation catalyst to obtain 1-tert-butyl-3,5-diisopropylbenzene;
   peroxidizing the 1-tert-butyl-3,5-diisopropylbenzene by gaseous oxygen in the presence of a peroxidation catalyst in a basic solution to obtain 1,3-di(peroxypropyl)-5-tert-butylbenzene;
   reducing the 1,3-di(peroxypropyl)-5-tert-butylbenzene with a reducing agent to 1,3-di(hydroxypropyl)-5-tert-butylbenzene; and
   chlorinating the 1,3-di(hydroxypropyl)-5-tert-butylbenzene to obtain 1,3-di(chloropropyl)-5-tert-butyl benzene.

2. The method according to claim 1, wherein the alkylation catalyst is an Iron(III) salt, such as, for example, $FeCl_3$.

3. The method according to claim 1, wherein said peroxidation catalyst in the basic solution is a Cobalt(II) salt and a tertiary amine in water.

4. The method according to claim 3, wherein the Cobalt(II) salt is $CoCl_2$ and the tertiary amine is pyridine.

5. The method according to claim 1, wherein the step of peroxidizing further includes the steps of:
   adjusting a pH of the 1,3-di(peroxypropyl)-5-tert-butylbenzene in solution with the addition of a base solution to a pH=10; and
   extracting the water phase with ether to provide a mixture containing 1,3-di(peroxypropyl)-5-tert-butylbenzene dissolved in ether.

6. The method according to claim 1, wherein the reducing agent is sodium sulfite.

7. The method according to claim 5, wherein the step of reducing includes reducing the mixture with sodium sulfite to provide 1,3-di(hydroxpropyl)-5-tert-butylbenzene,
   separating and extracting the water with additional ether; and
   evaporating and drying the 1,3-di(hydroxypropyl)-5-tert-butylbenzene.

8. The method according to claim 7, wherein the step of reducing further includes washing with hexane and recrystallizing with ethyl acetate the 1,3-di(hydroxpropyl)-5-tert-butylbenzene.

9. The method according to claim 1 wherein the step of chlorinating includes dissolving 1,3-di(hydroxypropyl)-5-tert-butylbenzene in methyl chloride to provide a solution and bubbling the solution in HCl.

10. The method according to claim 1, wherein the step of chlorinating includes purifying the 1,3-di(chloropropyl)-5-tert-butyl benzene by evaporating and recrystallizing the 1,3-di(chloropropyl)-5-tert-butyl benzene in hexane.

* * * * *